(12) United States Patent
Jiang et al.

(10) Patent No.: US 9,018,393 B2
(45) Date of Patent: Apr. 28, 2015

(54) METHOD FOR PREPARING 2-(N-SUBSTITUTED)-AMINO-BENZIMIDAZOLE DERIVATIVES

(75) Inventors: Yueheng Jiang, Jiangsu (CN); Tong Cai, Jiangsu (CN); Limin Que, Jiangsu (CN); Zhigang Lin, Jiangsu (CN)

(73) Assignee: ABA Chemicals Corporation, Jiangsu (CN)

( * ) Notice: Subject to any disclaimer, the term of this patent is extended or adjusted under 35 U.S.C. 154(b) by 0 days.

(21) Appl. No.: 13/976,865

(22) PCT Filed: Jan. 26, 2011

(86) PCT No.: PCT/CN2011/070638
§ 371 (c)(1),
(2), (4) Date: Sep. 9, 2013

(87) PCT Pub. No.: WO2012/088776
PCT Pub. Date: Jul. 5, 2012

(65) Prior Publication Data
US 2013/0345436 A1 Dec. 26, 2013

(51) Int. Cl.
C07D 235/30 (2006.01)
C07C 303/40 (2006.01)
C07D 235/14 (2006.01)

(52) U.S. Cl.
CPC ............ C07D 235/30 (2013.01); C07C 303/40 (2013.01); C07D 235/14 (2013.01)

(58) Field of Classification Search
USPC ........................................... 548/307.4, 307.7
See application file for complete search history.

(56) References Cited

U.S. PATENT DOCUMENTS

| 4,639,463 | A | * | 1/1987 | Rosner et al. ................. | 514/395 |
| 6,958,357 | B2 | * | 10/2005 | Hofmeister et al. .......... | 514/398 |
| 2008/0132551 | A1 | | 6/2008 | Rogers; Bruce Nelsen; et al. | |

FOREIGN PATENT DOCUMENTS

| CN | 1356899 A | 7/2002 |
| CN | 1478081 A | 2/2004 |
| JP | 2007191471 A | 8/2007 |

OTHER PUBLICATIONS

Sartori et al., Science of Synthesis, 2005, 18, pp. 665-758.*
Taha, et al.; Synthesis of some new heterobicyclic nitrogen systems bearing 7H-1, 2,4-triazolo[1,5-d]tetrazol-6-yl moiety for biological interest. Journal of the Chinese Chemical Society (Taipei, Taiwan), 2005, vol. 52, No. 1, pp. 137-140.
Carpenter, et al.; Carbodiimide-Based Benzimidazole Library Method; J. Comb. Chem.; 2006; 8; pp. 907-914.
Omar, et al.; The Cyclodesulfurization of Thio Compounds; XVI. Dicyclohexylcarbodiimide as an Efficient Cyclodesulfurizing Agent in the Synthesis of Heterocyclic Compounds from Various Thio Compounds;Synthesis; 1977, 864-865.
Cee, et al.; A one-pot method for the synthesis of 2-aminobenzimidazoles and related heterocycles; Tetrahedron Lett. 2006, 47, 3747-3750.
Perkins, et al.; Synthesis of 1-(Alkylamino)benzimidazoles; Tetrahedron Lett. 1999, 40, 1103-1106.
Seth, et al.; Efficient solution phase synthesis of 2-(N-acyl)-aminobenzimidazoles; Tetrahedron Lett. 2002, 43, 7303-7306.
Wang, et al.; A practical synthesis of 2-(N-substituted)-amino-benzimidazoles utilizing CuCl-promoted intramolecular cyclization of N-(2-aminoaryl)thioureas; Tetrahedron Lett. 2004, 45, 7167-7170.
Omar; The Cyclodesulfurization of Thio Compounds; VII. A New Facile Synthesis of N-Substituted Benzimidazoles; Synthesis 1974, 41-42.

* cited by examiner

*Primary Examiner* — Laura L. Stockton
(74) *Attorney, Agent, or Firm* — Stites & Harbison PLLC; Cong Ding

(57) ABSTRACT

A method for preparing 2-(N-substituted)-amino-benzimidazole derivatives is provided, which comprises the following steps: (1) reacting a compound of 2-(N-protecting group)-O-aryl diamine with a compound of N-phenoxycarbonyl monosubstituted amine to obtain a compound of 2-(N-protecting group)-amino aryl urea; (2) in a suitable organic solvent, performing dehydrating cyclization reaction of the compound of 2-(N-protecting group)-amino aryl urea in the presence of an organic base and dichloro triphenylphosphine prepared by triphenylphosphine oxide with oxalyl chloride or diphosgene or triphosgene, or dibromo triphenylphosphine prepared by triphenylphosphine oxide with bromine, to produce a compound of 1-protecting group-2-(N-substituted)-amino-benzimidazole; (3) deprotecting the resulting compound of 1-protecting group-2-(N-substituted)-amino-benzimidazole to obtain the compound 2-(N-substituted)-amino-benzimidazole.

7 Claims, No Drawings

METHOD FOR PREPARING 2-(N-SUBSTITUTED)-AMINO-BENZIMIDAZOLE DERIVATIVES

CROSS REFERENCE TO RELATED APPLICATION

This application is a §371 National State Application PCT/CN2011/070638, filed Jan. 26, 2011, which claims priority to CN201010606141.X, filed Dec. 27, 2010.

FIELD OF THE INVENTION

The invention relates to the field of preparation of pharmaceutical intermediates, and more particularly to a method for preparing 2-(N-substituted)-amino-benzimidazole derivatives.

BACKGROUND

Compounds including 2-amino-benzimidazole as a mother nucleus have an extensive value in application, which are very important intermediates of various drugs, weedicides, pesticides and the like, and also are primary pharmacophoric groups of a number of drug molecules, and thus they have wide spectrum drug effect.

In the field of medicine, due to the imidazole rings or heterocyclic benzimidazoles having certain pharmaceutical activities, such as anti-parasitic, anti-bacterial, anti-inflammatory, anticancer, sedative, and diuretic, the derivatives containing such functional structure have broad application prospects. For example, antineoplastic Denibulin, anthelmintic Mebendazole and Albendazole, antihistamine Emedastine, Astemizole, Norastemizole, Mizolastine etc.

The commonly used method for preparing 2-amino-benzimidazole derivatives is by means of the desulfuration and cyclization of 2-(2-aminoaryl) thiourea with disubstituted carbodiimide, however, highly toxic mercuric oxide, cuprous oxide, chlorine or methyl iodide are used in such method. Thus, many disadvantages exist in such method, such as, high cost, environmental pollution and complicated operation.

Another simple method for preparing 2-amino benzimidazole derivatives is to react the 2-chloro benzimidazole with aniline derivatives in the temperature of 140-150° C., but the yield is low and many by-products are generated in this method.

Such methods are as described in the following references: (1) J. Comb. Chem. 2006, 8, 907. (2) Synthesis 1977, 864-865. (3) Tetrahedron Lett. 2006, 47, 3747-3750. (4) Tetrahedron Lett. 1999, 40, 1103-1106. (5) Tetrahedron Lett. 2002, 43, 7303-7306. (6) Tetrahedron Lett. 2004, 45, 7167-7170. (7) Synthesis 1974, 41-42.

SUMMARY OF THE INVENTION

In order to overcome the above problems, a method for preparing 2-(N-substituted)-amino-benzimidazole derivatives is provided in the present invention, which has many advantages such as low cost, and convenient operation.

The technical solution employed in the invention is as follows: a method for preparing 2-(N-substituted)-amino-benzimidazole derivatives, comprising the steps of:

(1) reacting a compound of 2-(N-protecting group)—O-aryl diamine of formula II with a compound of N-phenoxycarbonyl monosubstituted amine of formula III to produce a compound of 2-(N-protecting group)-amino aryl urea of formula IV;

(2) dissolving the compound of 2-(N-protecting group)-amino aryl urea obtained in step (1) in an organic solvent and adding dichloro triphenylphosphine or dibromo triphenylphosphine to the resulting solution, then dehydrating cyclization reaction of the compound of 2-(N-protecting group)-amino aryl urea being carried out in the presence of an organic base to produce a compound of 1-protecting group-2-(N-substituted)-amino-benzimidazole, the organic solvent being selected from the group consisting of alkanes, aromatic hydrocarbons, halogenated aromatic hydrocarbons, nitriles, ethers and halogenated alkanes or any combination thereof;

(3) deprotecting the resulting compound of 1-protecting group-2-(N-substituted)-amino-benzimidazole obtained in step (2) to obtain the compound 2-(N-substituted)-amino-benzimidazole derivatives of formula I,

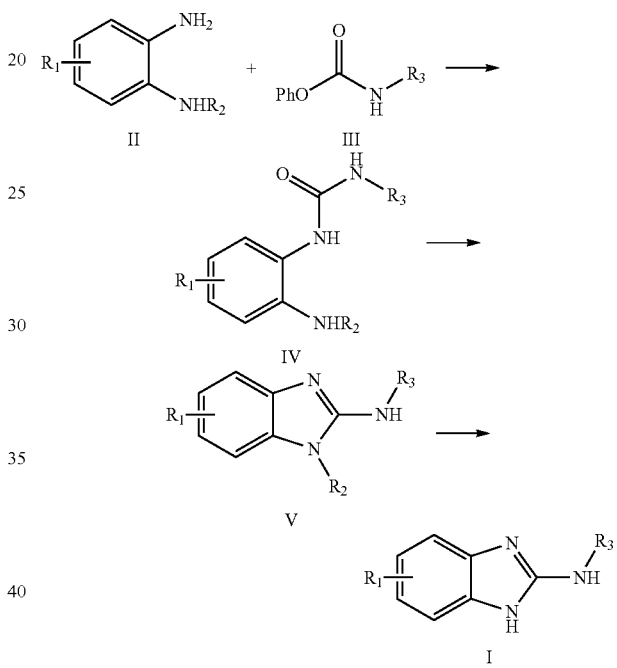

wherein the dichloro triphenylphosphine is prepared by triphenylphosphine oxide with oxalyl chloride or diphosgene or triphosgene, that is to say, in this step the fresh dichloro triphenylphosphine solution obtained from reaction of triphenylphosphine oxide with oxalyl chloride or diphosgene or triphosgene is used immediately; and wherein the dibromo triphenylphosphine is prepared by triphenylphosphine oxide with bromine, that is to say, in this step the fresh dibromo triphenylphosphine obtained from the reaction of triphenylphosphine oxide with bromine is used immediately.

Preferably, $R_1$ is selected from the group consisting of H, alkyl, aryl, aralkyl, halogen, alkoxy, alkylthio, aryloxy, arylthio, a cyano group, alkylcarbonyl, aroyl, or any combination thereof.

Preferably, $R_2$ is selected from the group of alkylsulfonyl, cycloalkyl sulfonyl, aryl sulfonyl, and trifluoroacetyl.

Preferably, $R_3$ is selected from the group of alkyl, aryl, aralkyl, cycloalkyl, cycloalkyl-alkyl, heteroaryl, heteroarylalkyl, and heterocycloalkyl.

More preferably, the organic solvent of step (2) is selected from the group consisting of toluene, xylene, chlorobenzene, acetonitrile, tetrahydrofuran, 1,4-dioxane, dichloromethane, chloroform, carbon tetrachloride, diethyl ether, propyl ether, isopropyl ether, methyl tert-butyl ether, hexane, cyclohexane, methyl cyclohexane, n-heptane, or any combination thereof.

Still more preferably, the organic base in step (2) is selected from the group of diethylamine, triethylamine, triethylene diamine, diisopropylethylamine, N-methyl morpholine, pyridine, 4-methylpyridine, and 4-dimethylaminopyridine.

Preferably, in the step (2) the molar ratio of dichloro triphenylphosphine or dibromo triphenylphosphine and 2-(N-protecting group)-amino aryl urea is 1:1 to 5:1, preferably 1:1 to 2:1.

More preferably, in the step (2) the molar ratio of the organic base and the 2-(N-protecting group)-amino aryl urea is 1:1 to 10:1, preferably 1:1 to 5:1.

Still more preferably, the dehydrating cyclization reaction is carried out in a temperature of −30~50° C., preferably −10-25° C.

Still more preferably, the dehydrating cyclization reaction is carried out in the range of 0.5~24 hours, preferably 1-10 hours.

In some embodiments wherein the compound 1-protecting group-2-(N-substituted)-amino-benzimidazole is deprotected by means of a conventional method, namely, the protecting group is removed in the presence of a base to obtain the compound 2-(N-substituted)-amino benzimidazole.

As compared with the prior art, the present invention has the following advantages: in the invention 2-(N-substituted)-amino-benzimidazole derivatives are prepared by means of intramolecular dehydrating cyclization of ureas containing relevant structures, such a method is applicable to industrial production because the raw materials are inexpensive and can be obtained easily, and the yield is low and the unit operation is simple.

DETAILED DESCRIPTION OF PREFERRED EMBODIMENTS

The present invention will be described in more detail hereinafter with reference to the various preferred embodiments. It is to be noted, however, that the embodiments are given only for illustrative purpose and therefore not to be considered as limiting of its scope, for the invention may admit to other equally effective embodiments.

Embodiment 1

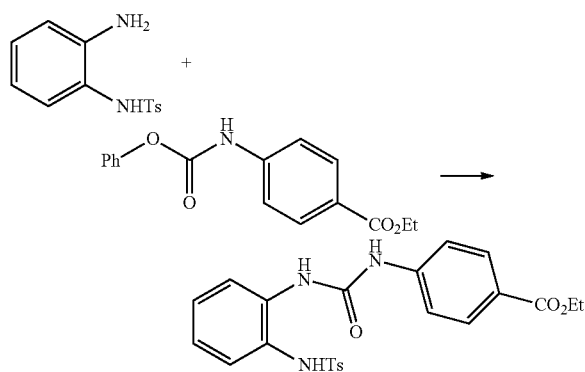

71.3 g (250 mmol) of 4-(carbophenoxyamino)-ethyl benzoate was dissolved in 500 ml dimethylsulfoxide (DMSO) and 68.9 g (262.5 mmol) of N—(2-aminophenyl)—p-toluenesulfonamide was slowly added to the above solution to obtain a reaction solution, and the reaction was carried out at room temperature for 60 mins, after the reaction was completed, 1000 ml of ethyl acetate was added, then the resulting solution was orderly washed by 500 ml of water, 500 ml of 1M hydrochloric acid, 250 ml of water, 500 ml of 1M sodium hydroxide and 100 ml of salt solution, subsequently the organic phase was dried by anhydrous sodium sulfate, and then after condensing and drying the obtained residual solid was recrystallized by n-hexane to obtain 100 g solid of disubstituted urea, the yield was 88%.

$^1$H NMR (400 MHz, DMSO-d6): δ 9.90 (s, 1H), 9.50 (s, 1H), 8.37 (s, 1H), 8.01 (dd, J=1.2, 8.0 Hz, 1H), 7.92 (ABq, J=8.8 Hz, 2H), 7.62 (ABq, J=8.8 Hz, 2H), 7.58 (ABq, J=8.0 Hz, 2H), 7.34 (ABq, J=8.0 Hz, 2H), 7.19 (dt, J=1.6, 8.0 Hz, 1H), 6.82 (dt, J=1.6, 8.0 Hz, 1H), 6.51 (dd, J=1.6, 8.0 Hz, 1H), 4.29 (q, J=7.2 Hz, 2H), 2.33 (s, 3H), 1.32 (t, J=7.2 Hz, 3H); $^{13}$C NMR (400 MHz, DMSO-d6): δ 165.4, 152.1, 144.4, 143.3, 136.5, 130.4, 129.5, 127.6, 127.3, 127.2, 125.3, 122.7, 122.3, 121.2, 117.2, 60.3, 20.9, 14.2.

Embodiment 2

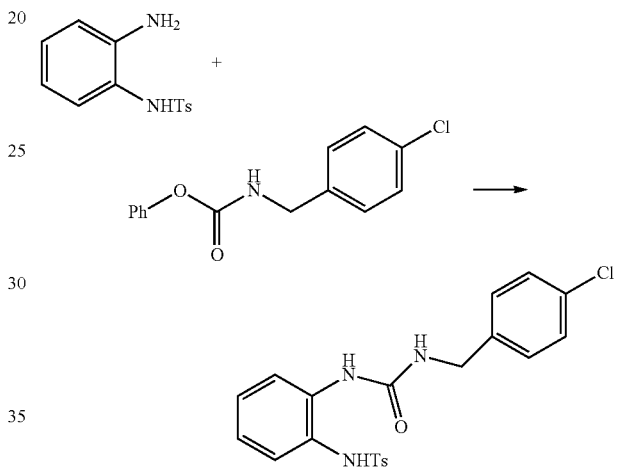

The same method as the embodiment 1 was utilized, but in which the 4-(carbophenoxyamino)-ethyl benzoate was replaced by 62 g (250 mmol) of 4-chlorobenzylamino phenyl formate, and 93.5 g solid of disubstituted urea was obtained, the yield was 90%.

$^1$H NMR (500 MHz, DMSO-d6): δ 9.47 (s, 1H), 8.12 (s, 1H), 7.85 (dd, J=0.5, 8.0 Hz, 1H), 7.53 (ABq, J=8.5 Hz, 2H), 7.52 (d, J=5.5 Hz, 1H), 7.42 (ABq, J=8.5 Hz, 2H), 7.36 (Abq, J=8.5 Hz, 2H), 7.33 (Abq, J=8.5 Hz, 2H), 7.11 (dt, J=1.0, 9.0 Hz, 1H), 6.77 (dt, J=1.0, 9.0 Hz, 1H), 6.59 (m, 1H), 4.29 (d, J=5.5 Hz, 2H), 2.37 (s, 3H); $^{13}$C NMR (500 MHz, DMSO-d6): δ 155.30, 143.1, 139.2, 136.7, 136.6, 131.3, 129.4, 129.1, 128.2, 127.2, 127.0, 126.9, 125.1, 121.7, 120.7, 42.2, 21.0.

Embodiment 3

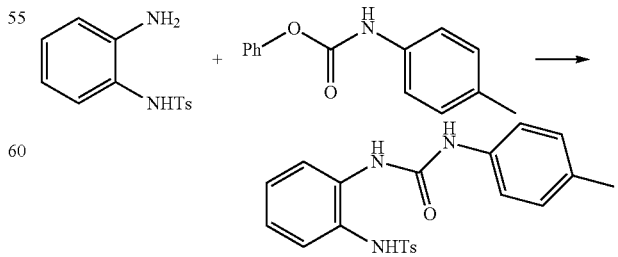

The same method as the embodiment 1 was utilized, but in which the 4-(carbophenoxyamino)-ethyl benzoate was replaced by 56.8 g (250 mmol) of p-tolylamino phenyl formate, and 91 g solid of disubstituted urea was obtained, the yield was 92%.

$^1$H NMR (400 MHz, DMSO-d6): δ 9.47 (s, 1H), 9.38 (s, 1H), 8.23 (s, 1H), 8.00 (dd, J=1.2, 8.0 Hz, 1H), 7.58 (ABq, J=8.0 Hz, 2H), 7.37 (ABq, J=8.0 Hz, 2H), 7.35 (Abq, J=8.0 Hz, 2H), 7.16 (dt, J=1.6, 8.4 Hz, 1H), 7.11 (Abq, J=8.0 Hz, 2H), 6.82 (dt, J=1.2, 7.6 Hz, 1H), 6.50 (dd, J=1.2, 8.0 Hz, 1H), 2.35 (s, 3H), 2.36 (s, 3H); $^{13}$C NMR (400 MHz, DMSO-d6): δ 152.5, 143.3, 137.2, 136.9, 136.4, 130.7, 129.5, 129.2, 127.5, 127.2, 127.1, 125.0, 121.8, 120.9, 118.3, 21.0, 20.3.

Embodiment 4

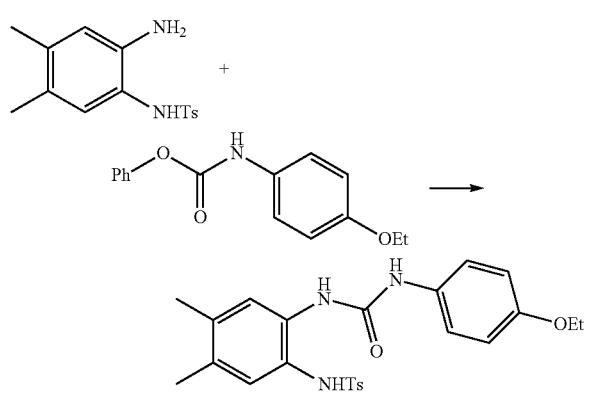

64.3 g of 4-oxethylphenylamino phenyl formate was dissolved in 500 ml dimethylsulfoxide (DMSO) and 76.2 g of N-(2-amino-4,5-dimethylphenyl)-p-toluenesulfonamide was slowly added to the above solution to obtain a reaction solution, and then the reaction was carried out at room temperature for 60 mins, after the reaction was completed, 1000 ml of ethyl acetate was added, then the resulting solution was orderly washed by 500 ml of water, 500 ml of 1M hydrochloric acid, 250 ml of water, 500 ml of 1M sodium hydroxide and 100 ml of salt solution, subsequently the organic phase was dried by anhydrous sodium sulfate, and then after condensing and drying the obtained residual solid was recrystallized by n-hexane to obtain 96.4 g solid of disubstituted urea, the yield was 85%.

$^1$H NMR (500 MHz, CDCl$_3$): δ 7.73 (s, 1H), 7.61 (ABq, J=8.0 Hz, 2H), 7.20 (s, 1H), 7.14 (ABq, J=8.0 Hz, 2H), 7.14 (s, 1H), 7.08 (Abq, J=8.0 Hz, 2H), 7.08 (d, J=5.0 Hz, 1H), 6.74 (Abq, J=8.0 Hz, 2H), 6.73 (s, 1H), 3.94 (q, J=7.0 Hz, 2H), 2.30 (s, 3H), 2.06 (s, 3H), 2.03 (s, 3H), 1.39 (t, J=7.0 Hz, 3H); $^{13}$C NMR (500 MHz, CDCl$_3$): δ 155.9, 154.7, 143.7, 136.5, 136.3, 133.7, 131.0, 130.5, 129.5, 128.1, 127.3, 125.7, 125.2, 123.3, 114.9, 63.7, 21.5, 19.3, 19.1, 14.8.

Embodiment 5

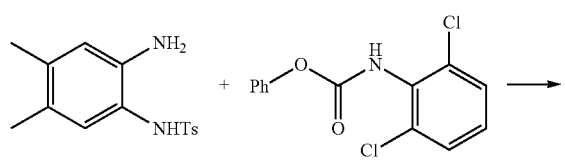

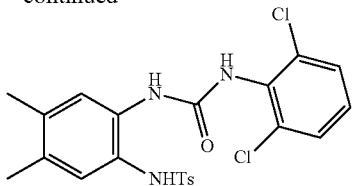

The same method as the embodiment 4 was utilized, but in which 4-oxethylphenylamino phenyl formate was replaced by 70.5 g of 2,6-dichlorophenylamino phenyl formate, and 107.6 g solid of disubstituted urea was obtained, the yield was 90%.

$^1$H NMR (500 MHz, DMSO-d6): δ 9.25 (s, 1H), 9.05 (s, 1H), 8.35 (s, 1H), 7.64 (s, 1H), 7.58 (d, J=8.0 Hz, 2H), 7.54 (ABq, J=8.5 Hz, 2H), 7.37 (ABq, J=8.5 Hz, 2H), 7.32 (t, J=8.0 Hz, 1H), 6.37 (s, 1H), 2.39 (s, 3H), 2.11 (s, 3H), 1.95 (s, 3H); $^{13}$C NMR (500 MHz, DMSO-d6): δ 152.6, 143.1, 136.7, 135.3, 133.9, 133.6, 133.2, 130.2, 129.4, 128.5, 128.4, 127.8, 127.1, 123.0, 122.1, 21.0, 19.2, 18.6.

Embodiment 6

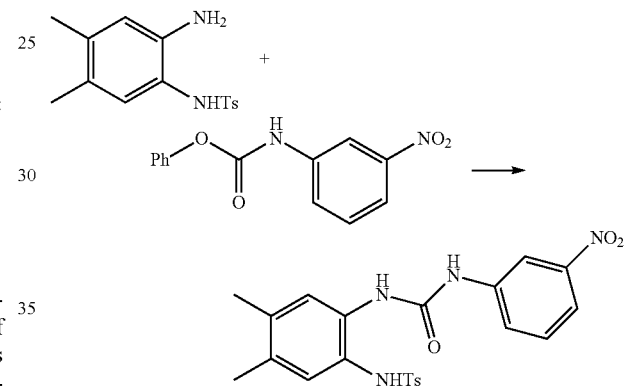

The same method as the embodiment 4 was utilized, but in which 4-oxethylphenylamino phenyl formate was replaced by 64.5 g of 3-nitrophenylamino phenyl formate, and 99 g solid of disubstituted urea was obtained, the yield was 87%.

$^1$H NMR (400 MHz, DMSO-d6): δ 9.89 (s, 1H), 9.35 (s, 1H), 8.56 (s, 1H), 8.12 (s, 1H), 7.83 (d, J=8.0 Hz, 1H), 7.72 (s, 1H), 7.71 (d, J=8.0 Hz, 1H), 7.60 (d, J=8.0 Hz, 1H), 7.55 (ABq, J=8.0 Hz, 2H), 7.32 (ABq, J=8.5 Hz, 2H), 6.30 (s, 1H), 2.30 (s, 3H), 2.15 (s, 3H), 1.95 (s, 3H); $^{13}$C NMR (400 MHz, DMSO-d6): δ 152.3, 148.1, 143.2, 141.2, 136.4, 135.6, 133.6, 130.5, 130.1, 129.4, 128.3, 127.1, 124.0, 123.1, 122.7, 116.2, 111.9, 20.9, 19.3, 18.6.

Embodiment 7

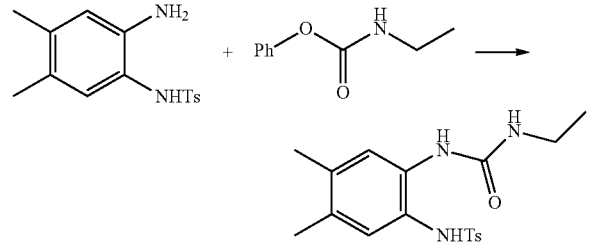

The same method as the embodiment 4 was utilized, but in which 4-oxethylphenylamino phenyl formate was replaced by 37.8 g of ethylamino phenyl formate, and 80 g solid of disubstituted urea was obtained, the yield was 92%.

¹H NMR (400 MHz, DMSO-d6): δ 9.39 (s, 1H), 7.75 (s, 1H), 7.51 (ABq, J=8.0 Hz, 2H), 7.40 (s, 1H), 7.33 (ABq, J=8.5 Hz, 2H), 6.69 (t, J=7.2 Hz, 1H), 6.47 (s, 1H), 3.08 (m, 2H), 2.37 (s, 3H), 2.09 (s, 3H), 1.96 (s, 3H), 1.06 (t, J=7.2 Hz, 3H); ¹³C NMR (400 MHz, DMSO-d6): δ 155.4, 143.0, 136.8, 135.0, 133.7, 129.8, 129.3, 127.9, 126.8, 123.1, 122.3, 34.1, 21.0, 19.2, 18.5, 15.3.

Embodiment 8

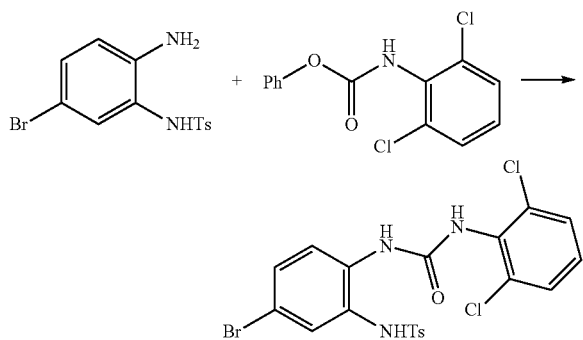

70.5 g of 2,6-dichlorophenylamino phenyl formate was dissolved in 500 ml dimethylsulfoxide (DMSO) and 90 g of N-(2-amino-5-bromophenyl)-p-toluenesulfonamide was slowly added to the above solution to obtain a reaction solution, and the reaction was carried out at room temperature for 60 mins, after the reaction was completed, 1000 ml of ethyl acetate was added, and the resulting solution was orderly washed by 500 ml of water, 500 ml of 1M hydrochloric acid, 250 ml of water, 500 ml of 1M sodium hydroxide and 100 ml of salt solution, then the organic phase was dried by anhydrous sodium sulfate, and after condensing and drying the obtained residual solid was recrystallized by n-hexane to obtain 117 g solid of disubstituted urea, the yield was 89%.

¹H NMR (400 MHz, DMSO-d6): δ 9.56 (s, 1H), 9.41 (s, 1H), 8.66 (s, 1H), 8.31 (s, 1H), 7.60 (d, J=8.0 Hz, 2H), 7.56 (ABq, J=8.0 Hz, 2H), 7.40 (ABq, J=8.5 Hz, 2H), 7.34 (t, J=8.0 Hz, 1H), 7.98 (d, J=8.4 Hz, 1H), 7.39 (d, J=8.4 Hz, 1H), 2.39 (s, 3H); ¹³C NMR (400 MHz, DMSO-d6): δ 152.2, 143.5, 138.7, 135.9, 133.8, 132.8, 129.7, 129.0, 128.7, 128.5, 127.2, 124.4, 123.7, 122.1, 120.4, 21.0.

Embodiment 9

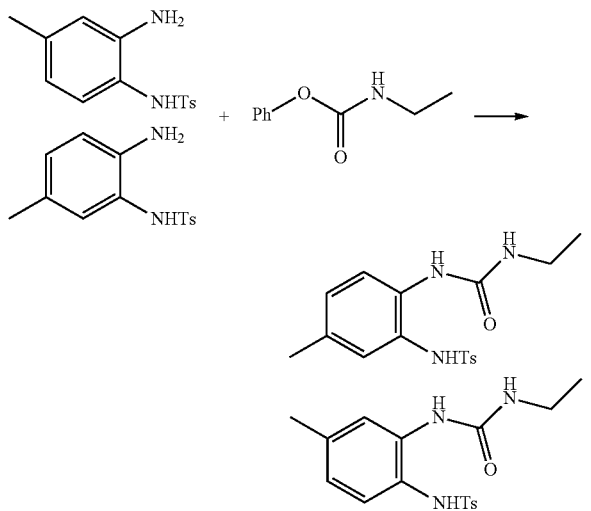

37.8 g of ethylamino phenyl formate was dissolved in 500 ml dimethylsulfoxide (DMSO) and 72.5 g mixture of N-(2-amino-4-methylphenyl)-p-toluenesulfonamide with N-(2-amino-5-methylphenyl)-p-toluenesulfonamide (1:1) was slowly added to the above solution to obtain a reaction solution, and then the reaction was carried out at room temperature for 60 mins, after the reaction was completed, 1000 ml of ethyl acetate was added, then the resulting solution was orderly washed by 500 ml of water, 500 ml of 1M hydrochloric acid, 250 ml of water, 500 ml of 1M sodium hydroxide and 100 ml of salt solution, subsequently the organic phase was dried by anhydrous sodium sulfate, and after condensing and drying the obtained residual solid was recrystallized by n-hexane to obtain 73 g solid mixture of 4-methyl disubstituted urea with 5-methyl disubstituted urea (1:1), the yield was 87%.

¹H NMR (500 MHz, DMSO-d6): δ 9.39-9.47 (m, 2H), 7.83-7.86 (m, 2H), 7.64 (s, 1H), 7.51-7.54 (m, 4H), 7.33-7.35 (m, 4H), 6.90-6.92 (m, 2H), 6.71-3.73 (m, 1H), 6.56-6.57 (m, 1H), 6.51-6.56 (m, 1H), 6.45-6.46 (m, 1H), 3.07-3.11 (m, 4H), 2.37 (s, 6H), 2.18 (s, 3H), 2.06 (s, 3H), 1.06-1.08 (m, 6H); ¹³C NMR (125 MHz, DMSO-d6): δ 155.47, 155.17, 143.07, 143.04, 136.77, 136.71, 136.68, 136.65, 133.46, 131.01, 129.42, 129.36, 127.56, 127.18, 126.96, 126.85, 125.55, 122.32, 122.18, 121.17, 121.04, 34.14, 34.09, 20.98, 20.96, 20.87, 20.07, 15.25, 15.22.

Embodiment 10

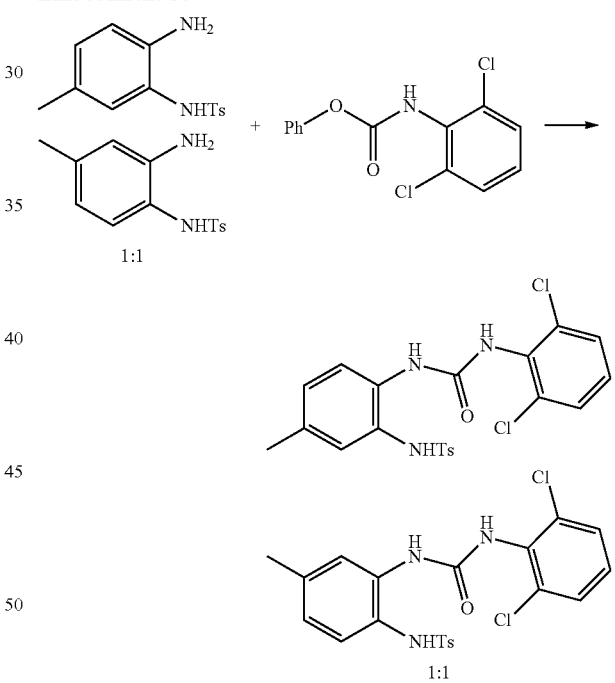

The same method as the embodiment 9 was utilized, but in which the ethylamino phenyl formate was replaced by 70.5 g of 2,6-dichlorobenzylamino phenyl formate, and 98.6 g solid of disubstituted urea was obtained, the yield was 85%.

Embodiment 11

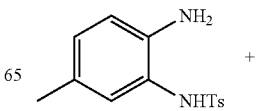

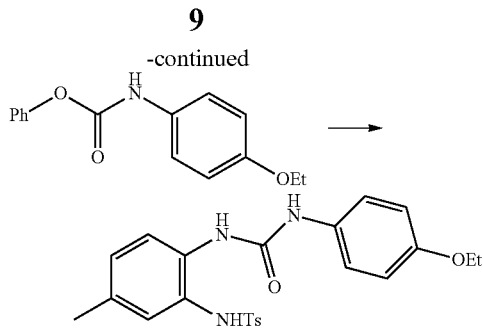

The same method as the embodiment 4 was utilized, but in which the N-(2-amino-4,5-dimethylphenyl)—p-toluenesulfonamide was replaced by 72.5 g of N-(2-amino-5-methylphenyl)—p-toluenesulfonamide, and 95.6 g solid of disubstituted urea was obtained, the yield was 87%.

¹H NMR (500 MHz, CDCl₃): δ 9.36 (s, 1H), 9.14 (s (1H), 8.35 (s, 1H), 8.04 (s (1H), 7.75 (d, J=2.0 Hz, 1H), 7.55 (ABq, J=8.0 Hz, 2H), 7.36 (ABq, J=8.0 Hz, 2H), 7.32 (ABq, J=8.0 Hz, 2H), 6.95 (d, J=2.0 Hz, 1H), 6.83 (ABq, J=8.0 Hz, 2H), 3.95 (q, J=7.0 Hz, 2H), 2.35 (s, 3H), 2.21 (s, 3H), 1.32 (t, J=7.0 Hz, 3H).

Embodiment 12

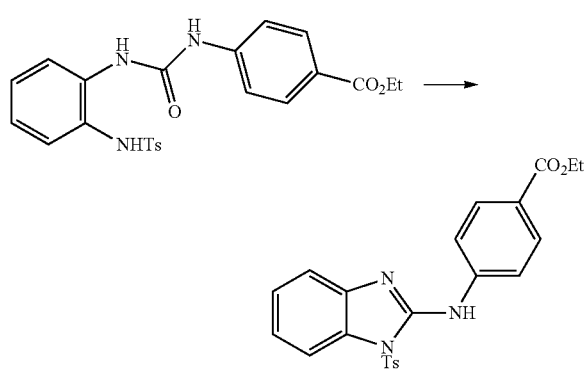

27.8 g (100 mmol) of triphenylphosphine oxide was dissolved in 150 ml acetonitrile and the solution was cooled to 0~5° C., and 130 g (102 mmol) of oxalyl chloride was slowly and dropwise added to the cooled solution under stirring to obtain a reaction solution, and then the reaction solution was still stirred for 15 mins to obtain a solution of dichloro triphenylphosphine. 44.4 g (98 mmol) of the disubstituted urea obtained in embodiment 1 and 20.2 g (200 mmol) triethylamine were suspended in 50 ml acetonitrile, the suspension was slowly added to the above solution of dichloro triphenylphosphine in the temperature of 0-5° C., then the reaction was still carried out for 0.5-5 hours. After the reaction was completed, 200 ml water was added and the organic phase was extracted by 500 ml of ethyl acetate, and then the solution containing organic phase was condensed to 50 ml and 100 ml of isopropanol was added, subsequently 33 ml water was dropwise added in the temperature of 40-50° C., then the final solution was cooled to room temperature and stirred for 2-5 hours, followed by filtered and dried to obtain 32 g of 4-(1-p-toluenesulfonyl-1H-benzimidazolyl-2-amino) ethyl benzoate, the yield was 75%.

¹H NMR (400 MHz, CDCl₃): δ 8.94 (br, 1H), 8.12 (t, 4.4 Hz, 1H), 7.88 (dd, J=1.6, 7.2 Hz, 2H), 7.78-7.80 (m, 3H), 7.50 (d, J=7.2 Hz, 1H), 7.26-7.29 (m, 3H), 7.17-7.25 (m, 1H), 4.40 (dd, J=7.0, 14.4 Hz, 2H), 2.35 (s, 3H), 1.42 (t, J=7.2 Hz, 3H);

¹³C NMR (100 MHz, CDCl₃): δ 166.3, 146.8, 146.4, 142.4, 142.0, 134.1, 131.7, 130.4, 129.4, 126.9, 125.3, 124.8, 119.8, 118.5, 117.9, 112.8, 60.8, 21.7, 14.4.

Embodiment 13

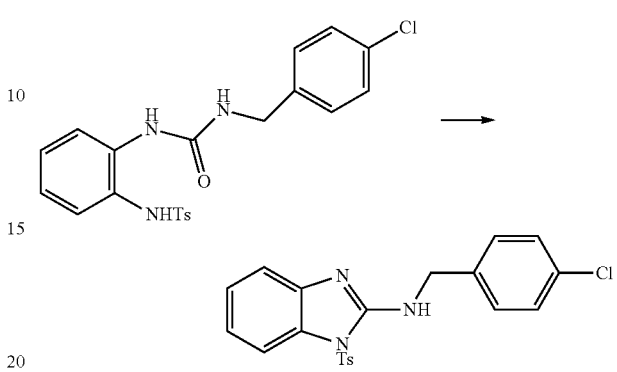

The same method as the embodiment 12 was utilized, but in which the disubstituted urea obtained in embodiment 1 was replaced by 40.7 g disubstituted urea obtained in embodiment 2, and 32.7 g of N-(4-chlorophenylmethyl)-1-p-toluenesulfonyl-1H-benzimidazolyl-2-amine was obtained, the yield was 84%.

¹H NMR (400 MHz, CDCl₃): δ 7.71-7.76 (m, 3H), 7.28-7.36 (m, 5H), 7.18-7.24 (m, 3H), 7.08-7.12 (m, 1H), 6.74 (br, 1H), 4.73 (d, J=6.0 Hz, 2H), 2.38 (s, 3H); ¹³C NMR (100 MHz, CDCl₃): δ 151.9, 146.1, 142.5, 136.6, 134.3, 133.5, 130.9, 130.1, 129.1, 128.9, 126.8, 124.9, 121.7, 117.6, 112.8, 46.4, 31.7.

Embodiment 14

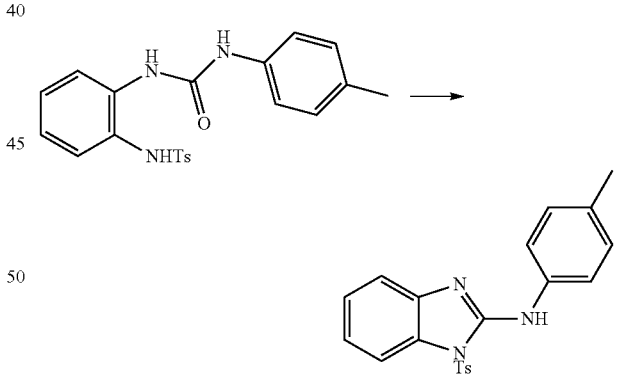

The same method as the embodiment 12 was utilized, but in which the disubstituted urea obtained in embodiment 1 was replaced by 38.8 g disubstituted urea obtained in embodiment 3, and 32.2 g of N-p-methylphenyl-1-p-toluenesulfonyl-1H-benzimidazolyl-2-amine was obtained, the yield was 87%.

¹H NMR (400 MHz, CDCl₃): δ 8.56 (br, 1H), 7.74-7.78 (m, 3H), 7.60-7.62 (m, 2H), 7.39 (d, J=7.6 Hz, 1H), 7.17-7.20 (m, 5H), 7.08-7.12 (m, 1H), 2.33 (s, 3H), 2.29 (s, 3H); ¹³C NMR (100 MHz, CDCl₃): δ 148.2, 146.2, 142.5, 135.9, 134.3, 133.1, 130.3, 130.1, 128.8, 126.9, 124.1, 122.1, 119.5, 117.7, 112.7, 21.6, 20.9.

Embodiment 15

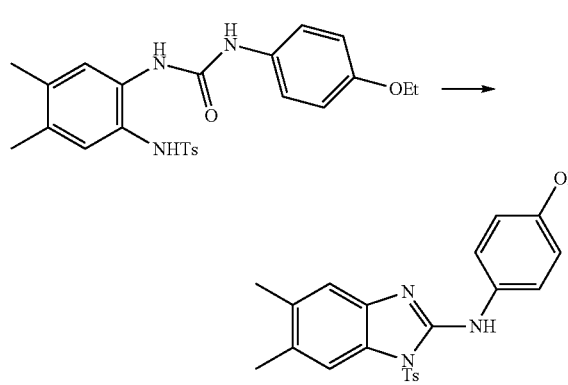

The same method as the embodiment 12 was utilized, but in which the disubstituted urea obtained in embodiment 1 was replaced by 44.4 g disubstituted urea obtained in embodiment 4, and 35 g of N-(4-oxyethylphenyl)-5,6-dimethyl-1-p-toluenesulfonyl-1H-benzimidazolyl-2-amine was obtained, the yield was 82%.

$^1$H NMR (400 MHz, CDCl$_3$): δ 8.42 (br, 1H), 7.80-7.82 (m, 2H), 7.62 (dd, J=2.0, 6.4 Hz, 1H), 7.51 (s, 1H), 7.23-7.25 (m, 2H), 7.20 (s, 1H), 6.94-6.96 (m, 2H), 4.05 (dd, J=6.8, 14.0 Hz, 2H), 2.35 (s, 6H), 2.28 (s, 3H), 1.44 (t, J=7.2 Hz, 3H); $^{13}$C NMR (100 MHz, CDCl$_3$): δ 155.4, 148.2, 145.9, 140.7, 134.4, 133.6, 131.7, 130.6, 130.2, 128.4, 126.8, 121.2, 118.3, 116.2, 113.5, 63.8, 21.6, 20.3, 20.1, 14.8.

Embodiment 16

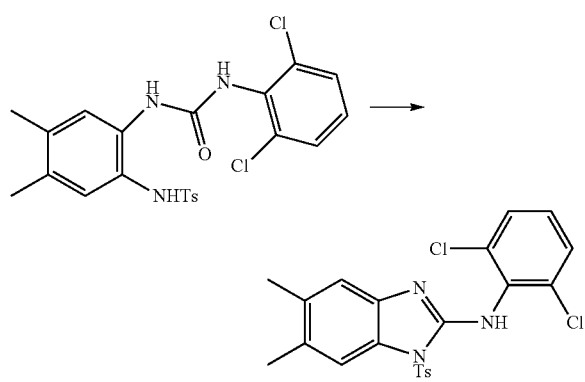

The same method as the embodiment 12 was utilized, but in which the disubstituted urea obtained in embodiment 1 was replaced by 46.9 g disubstituted urea obtained in embodiment 5, and 40.6 g of N-(2,6-dichlorophenyl)-5,6-dimethyl-1-p-toluenesulfonyl-1H-benzimidazolyl-2-amine was obtained, the yield was 90%.

$^1$H NMR (500 MHz, CDCl$_3$): δ 7.99-8.01 (m, 2H), 7.91 (br, 1H), 7.60 (s, 1H), 7.41-7.43 (m, 2H), 7.29-7.31 (m, 2H), 7.17-7.21 (m, 2H), 2.39 (s, 3H), 2.35 (s, 3H), 2.25 (s, 3H); 13C NMR (125 MHz, CDCl$_3$): δ 147.6, 146.1, 139.8, 134.6, 133.4, 133.3, 133.1, 131.0, 130.1, 129.3, 128.8, 127.9, 118.7, 113.1, 21.6, 20.3, 20.0.

Embodiment 17

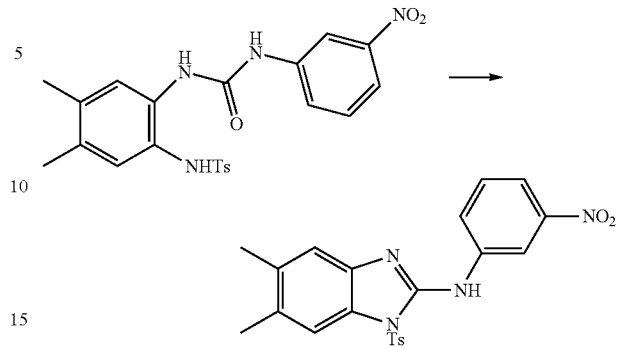

The same method as the embodiment 12 was utilized, but in which the disubstituted urea obtained in embodiment 1 was replaced by 44.5 g disubstituted urea obtained in embodiment 6, and 32.9 g of N-(3-nitrophenyl)-5,6-dimethyl-1-p-toluenesulfonyl-1H-benzimidazolyl-2-amine was obtained, the yield was 77%.

$^1$H NMR (500 MHz, CDCl$_3$): δ 8.84 (br, 1H), 8.74 (t, J=2.0 Hz, 1H), 8.05 (dd, J=1.5, 8.0 Hz, 1H), 7.89 (dd, J=1.5, 8.0 Hz, 1H), 7.75-7.77 (m, 2H), 7.49-7.53 (m, 2H), 7.23-7.25 (m, 3H), 2.33 (d, J=2.5 Hz, 6H), 2.27 (s, 3H); $^{13}$C NMR (125 MHz, CDCl$_3$): δ 148.9, 146.3, 146.2, 139.9, 139.8, 134.2, 134.0, 131.7, 130.3, 129.8, 128.1, 126.7, 124.2, 118.9, 117.4, 113.4, 113.3, 21.6, 20.3, 20.0.

Embodiment 18

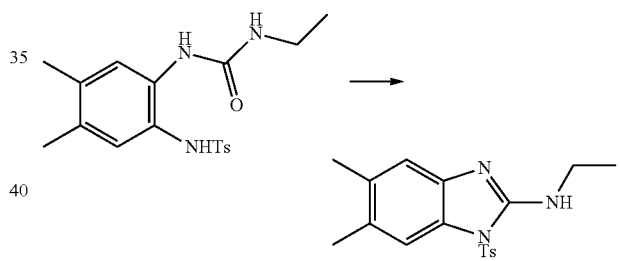

The same method as the embodiment 12 was utilized, but in which the disubstituted urea obtained in embodiment 1 was replaced by 34 g disubstituted urea obtained in embodiment 7, and 26.5 g of N-ethyl-5,6-dimethyl-1-p-toluenesulfonyl-1H-benzimidazolyl-2-amine was obtained, the yield was 82%.

$^1$H NMR (400 MHz, CDCl$_3$): δ 7.74-7.76 (m, 2H), 7.46 (s, 1H), 7.22-7.26 (m, 2H), 7.08 (s, 1H), 6.26 (br, 1H), 3.51-3.58 (m, 2H), 2.34 (s, 3H), 2.29 (s, 3H), 2.23 (s, 3H), 1.32 (t, J=7.2 Hz, 3H); $^{13}$C NMR (100 MHz, CDCl$_3$): δ 151.7, 145.7, 140.9, 134.6, 133.2, 130.1, 129.6, 128.9, 126.8, 117.5, 113.1, 38.1, 21.6, 20.2, 20.0, 14.9.

Embodiment 19

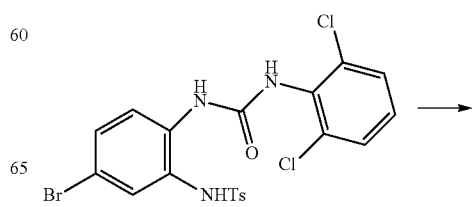

-continued

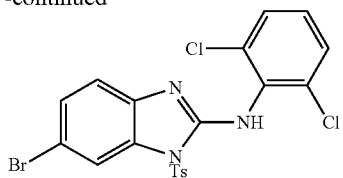

The same method as the embodiment 12 was utilized, but in which the disubstituted urea obtained in embodiment 1 was replaced by 52 g disubstituted urea obtained in embodiment 8, and 45.1 g of N-(2,6-dimethylphenyl)-6-bromo-1-p-toluenesulfonyl-1H-benzimidazolyl-2-amine was obtained, the yield was 90%.

¹H NMR (500 MHz, CDCl₃): δ 7.99 (br, 1H), 7.94-7.96 (m, 2H), 7.64 (d, J=8.5 Hz, 1H), 7.47 (d, J=1.5 Hz, 1H), 7.40-7.42 (m, 2H), 7.29-7.31 (m, 2H), 7.19-7.25 (m, 2H), 2.38 (s, 3H); ¹³C NMR (125 MHz, CDCl₃): δ 149.1, 146.6, 143.3, 134.1, 133.4, 132.6, 130.3, 130.0, 128.9, 128.5, 127.4, 125.0, 121.1, 117.9, 113.5, 21.7.

Embodiment 20

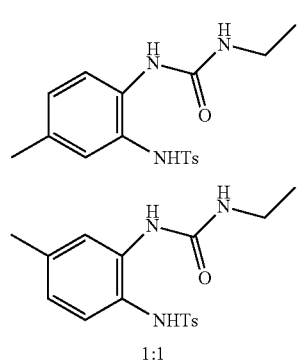

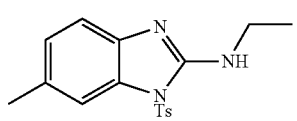

The same method as the embodiment 12 was utilized, but in which the disubstituted urea obtained in embodiment 1 was replaced by 32.7 g disubstituted urea obtained in embodiment 9, and 26 g mixture of N, 5-dimethyl-1-p-toluenesulfonyl-1H-benzimidazolyl-2-amine with N, 6-dimethyl-1-p-toluenesulfonyl-1-H-benzimidazolyl-2-amine (1:1) was obtained, the yield was 84%.

¹H NMR (400 MHz, CDCl₃): δ 7.76-7.79 (m, 4H), 7.53-7.58 (m, 2H), 7.19-7.28 (m, 4H), 7.12 (s, 1H), 6.97-6.99 (m, 1H), 6.85-6.88 (m, 1H), 6.32-6.38 (m, 2H), 3.54-3.61 (m, 4H), 2.41 (s, 2H), 2.36 (s, 2H), 1.32-1.36 (t, J=7.2 Hz, 6H); ¹³C NMR (125 MHz, CDCl₃): δ 152.9, 150.9, 133.9, 128.6, 121.3, 120.5, 118.8, 115.7, 114.6, 109.4, 106.7, 63.2, 21.2, 14.7.

Embodiment 21

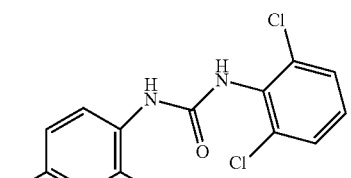

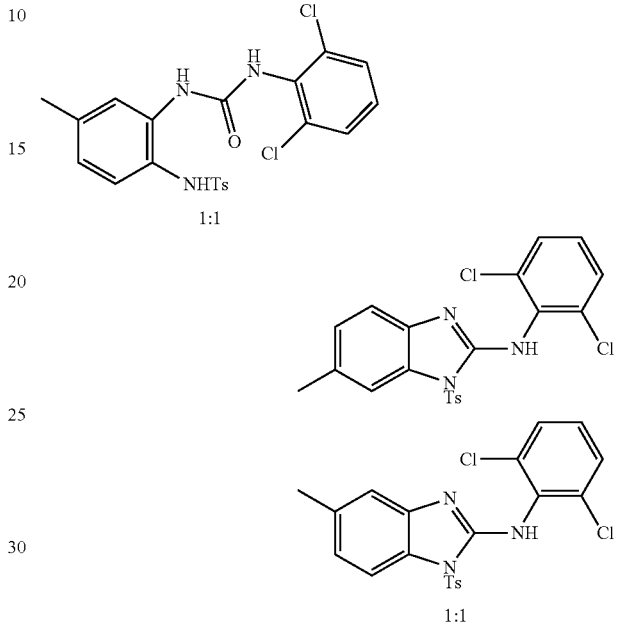

The same method as the embodiment 12 was utilized, but in which the disubstituted urea obtained in embodiment 1 was replaced by 45.5 g disubstituted urea obtained in embodiment 10, and 36.3 g mixture of N-(2,6-dimethylphenyl)-5-methyl-1-p-toluenesulfonyl-1H-benzimidazolyl-2-amine with N-(2,6-dimethylphenyl)-6-methyl-1-p-toluenesulfonyl-1-H-benzimidazolyl-2-amine (1:1) was obtained, the yield was 83%.

Embodiment 22

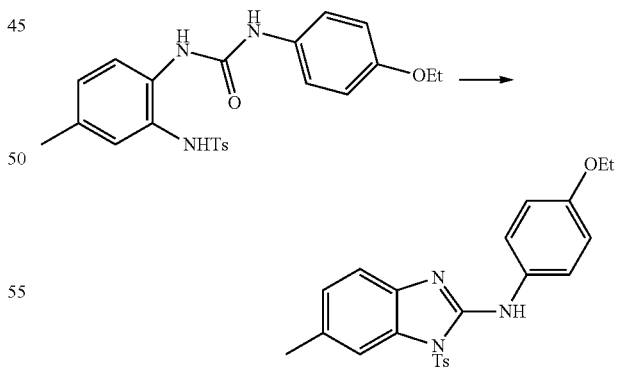

27.8 g (100 mmol) of triphenylphosphine oxide was dissolved in 150 ml acetonitrile and the solution was cooled to 0~5° C., and 16.5 g (102 mmol) of bromine was slowly added to the cooled solution under stirring to obtain a reaction solution, and then the reaction solution was still stirred for 15 mins to obtain a solution of dibromo triphenylphosphine oxide. 44.4 g (98 mmol) of the disubstituted urea obtained in embodiment 11 and 20.2 g (200 mmol) triethylamine were suspended in 50 ml acetonitrile, the suspension was slowly added to the above solution of dibromo triphenylphosphine oxide in the temperature of 0-5° C., then the reaction was still carried out for 0.5-5 hours. After the reaction was completed, 200 ml water was added and the organic phase was extracted by 500 ml of ethyl acetate, and then the solution containing organic phase was condensed to 50 ml and next 100 ml isopropanol was added, subsequently 33 ml water was dropwise added in the temperature of 40-50° C., then the final solution was cooled to room temperature and stirred for 2-5 hours, followed by filtered and dried to obtain 31 g of N-(4-oxyphenyl)-6-methyl-p-toluenesulfonyl-1H-benzimidazolyl-2-amine, the yield was 77%.

$^1$H NMR (400 MHz, CDCl$_3$): δ 8.41 (br, 1H), 7.75-7.79 (m, 2H), 7.56-7.61 (m, 3H), 7.18-7.25 (m, 3H), 6.89-6.92 (m, 3H), 3.99-4.04 (m, 2H), 2.35 (s, 3H), 2.31-2.33 (m, 3H), 1.40 (t, J=11.2 Hz, 3H).

Embodiment 23

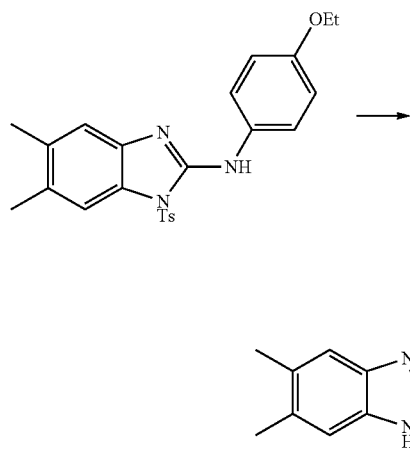

21.8 g (50 mmol) of N-(4-oxyethylphenyl)-5,6-dimethyl-1-p-toluenesulfonyl-1H-benzimidazolyl-2-amine obtained in embodiment 15 was dissolved in a mixed solvent of 100 ml methanol and 50 ml tetrahydrofuran and then 70 ml (350 mmol) of 5M sodium hydroxide was added to the above solution, subsequently the resulting solution was stirred at room temperature for 10-30 mins and next 200 ml water was added, then the organic phase was extracted using 200 ml ethyl acetate, the obtained residual solid after condensing and drying was recrystallized using methyl tert-butyl ether, and 12.7 g of N-(4-oxyethylphenyl)-5,6-dimethyl-1H-benzimidazolyl-2-amine was obtained, the yield was 90%.

$^1$H NMR (400 MHz, DMSO-d6): δ 10.62 (br, 1H), 8.99 (br, 1H), 7.55-7.57 (m, 2H), 9.05 (s, 2H), 6.85-6.87 (m, 2H), 3.95 (q, J=6.8 Hz, 2H), 2.23 (s, 6H), 1.29 (t, J=6.8 Hz, 3H); $^{13}$C NMR (100 MHz, DMSO-d6): δ 152.8, 150.6, 134.2, 137.2, 127.5, 118.6, 116.6, 114.7, 110.0, 63.2, 19.9, 14.7.

Embodiment 24

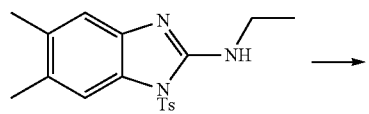

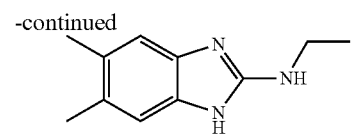

17.2 g (50 mmol) of N-ethyl-5,6-dimethyl-1-p-toluenesulfonyl-1H-benzimidazolyl-2-amine obtained in embodiment 18 was dissolved in a mixed solvent of 100 ml methanol and 50 ml tetrahydrofuran and then 70 ml (350 mmol) of 5M sodium hydroxide was added to the above solution, then the resulting solution was stirred at room temperature for 10-30 mins and next 200 ml water was added, then the organic phase was extracted using 200 ml ethyl acetate, the obtained residual solid after condensing and drying was recrystallized using methyl tert-butyl ether, and 8.7 g of N-ethyl-5,6-dimethyl-1H-benzimidazolyl-2-amine was obtained, the yield was 92%.

$^1$H NMR (400 MHz, DMSO-d6): δ 8.77 (br, 1H), 6.97 (s, 2H), 6.02 (br, 1H), 3.45-3.48 (m, 2H), 2.10 (s, 6H), 1.07 (t, J=7.0 Hz, 3H).

Embodiment 25

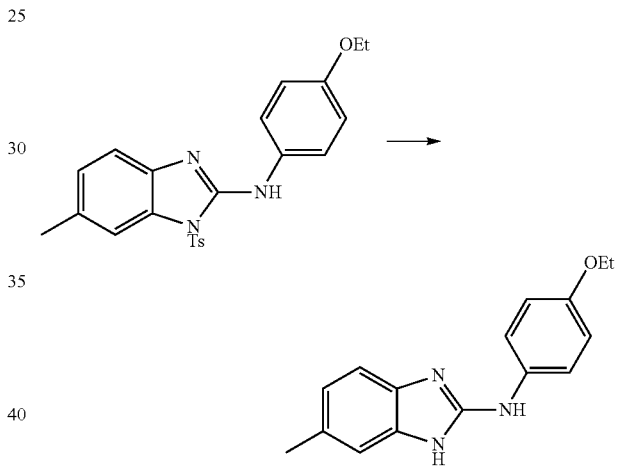

21.1 g (50 mmol) of N-(4-oxyethylphenyl)-6-methyl-1-p-toluenesulfonyl-1H-benzimidazolyl-2-amine obtained in embodiment 22 was dissolved in a mixed solvent of 100 ml methanol and 50 ml tetrahydrofuran and then 70 ml (350 mmol) of 5M sodium hydroxide was added to the above solution, subsequently the resulting solution was stirred at room temperature for 10-30 mins and next 200 ml water was added, then the organic phase was extracted using 200 ml ethyl acetate, the obtained residual solid after condensing and drying was recrystallized using methyl tert-butyl ether, and 12.3 g of N-(4-oxyethylphenyl)-6-methyl-1H-benzimidazolyl-2-amine was obtained, the yield was 92%.

$^1$H NMR (400 MHz, DMSO-d6): δ 10.72 (br, 1H), 9.06 (br, 1H), 7.56-7.58 (m, 2H), 7.07-7.13 (m, 2H), 6.86-6.88 (m, 2H), 6.78 (d, J=7.2 Hz, 1H), 3.93-3.98 (m, 2H), 2.33 (s, 3H), 1.29 (t, J=11.2 Hz, 3H); $^{13}$C NMR (100 MHz, DMSO-d6): δ 152.9, 150.9, 133.9, 128.6, 121.3, 120.5, 118.8, 115.7, 114.6, 109.4, 106.7, 63.2, 21.2, 14.7.

As described above, the specific embodiments are illustrated according to the spirit of the invention, but the invention is not limited to the aforementioned embodiments and implementing methods. Many variations and implements can be made within the scope of the invention by those skilled in the related art.

What is claimed is:

1. A method for preparing 2-(N-substituted)-amino-benzimidazole derivatives, comprising the steps of:

(1) reacting a compound of 2-(N-protecting group)-O-aryl diamine of the following formula II:

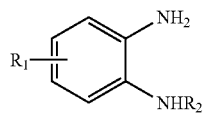
(II)

with a compound of N-phenoxycarbonyl monosubstituted amine of the following formula III:

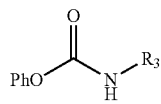
(III)

to produce a compound of 2-(N-protecting group)-amino aryl urea of the following formula IV:

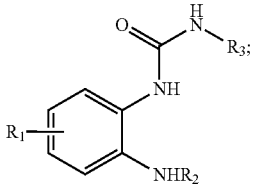
(IV)

(2) dissolving the compound of 2-(N-protecting group)-amino aryl urea obtained in step (1) in an organic solvent and adding dichloro triphenylphosphine or dibromo triphenylphosphine to the resulting solution, then performing a dehydrating cyclization reaction of the compound of 2-(N-protecting group)-amino aryl urea in the presence of an organic base to produce a compound of 1-protecting group-2-(N-substituted)-amino-benzimidazole of the following formula V:

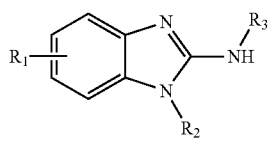
(V)

the organic solvent being selected from the group consisting of alkanes, aromatic hydrocarbons, halogenated aromatic hydrocarbons, nitriles, ethers and halogenated alkanes, or any combination thereof; and (3) deprotecting the compound of 1-protecting group-2-(N-substituted)-amino-benzimidazole obtained in step (2) to obtain a compound of 2-(N-substituted)-amino-benzimidazole derivatives of the following formula I:

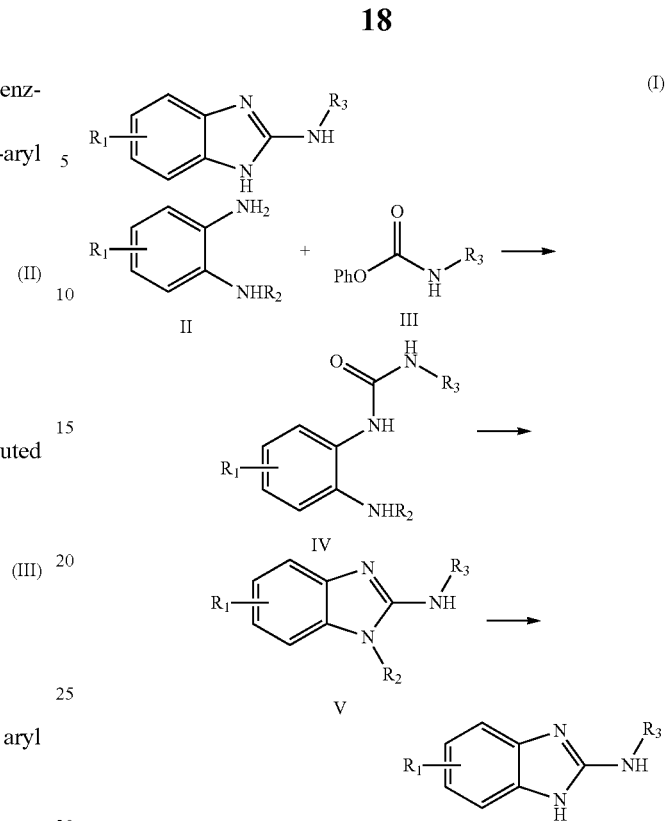

wherein
$R_1$ is selected from the group consisting of H, alkyl, aryl, aralkyl, halogen, alkoxy, alkylthio, aryloxy, arylthio, a cyano group, alkylcarbonyl, aroyl, and any combination thereof, $R_2$ is selected from the group consisting of of alkylsulfonyl, cycloalkyl sulfonyl, aryl sulfonyl, and trifluoroacetyl, and $R_3$ is selected from the group consisting of alkyl, aryl, aralkyl, cycloalkyl, cycloalkyl-alkyl, heteroaryl, heteroarylalkyl, and hetercycloalkyl;

wherein the dichloro triphenylphosphine is prepared by triphenylphosphine oxide with oxalyl chloride or diphosgene or triphosgene; and wherein the dibromo triphenylphosphine is prepared by triphenylphosphine oxide with bromine.

2. The method for preparing 2-(N-substituted)-amino-benzimidazole derivatives as claimed in claim 1, wherein the organic solvent of step (2) is selected from the group consisting of toluene, xylene, chlorobenzene, acetonitrile, tetrahydrofuran, 1,4-dioxane, dichloromethane, chloroform, carbon tetrachloride, ethyl ether, propyl ether, isopropyl ether, methyl tert-butyl ether, hexane, cyclohexane, methyl cyclohexane, n-heptane, and combinations thereof.

3. The method for preparing 2-(N-substituted)-amino-benzimidazole derivatives as claimed in claim 1, wherein the organic base in step (2) is selected from the group consisting of diethylamine, triethylamine, triethylene diamine, diisopropylethylamine, N-methyl morpholine, pyridine, 4-methylpyridine, and 4-dimethylaminopyridine.

4. The method for preparing 2-(N-substituted)-amino-benzimidazole derivatives as claimed in claim 1, wherein in the step (2) the molar ratio of the dichloro triphenylphosphine or dibromo triphenylphosphine and 2-(N-protecting group)-amino aryl urea is 1:1 to 5:1.

5. The method for preparing 2-(N-substituted)-amino-benzimidazole derivatives as claimed in claim 1, wherein in the step (2) the molar ratio of the organic base and the 2-(N-protecting group)-amino aryl urea is 1:1 to 10:1.

6. The method for preparing 2-(N-substituted)-amino-benzimidazole derivatives as claimed in claim 1, wherein the dehydrating cyclization reaction is carried out in a temperature of about −30° C. to about 50° C.

7. The method for preparing 2-(N-substituted)-amino-benzimidazole derivatives as claimed in claim 1, wherein the dehydrating cyclization reaction is carried out in the range of about 0.5 to about 24 hours.

* * * * *